(12) United States Patent
Matsuoka et al.

(10) Patent No.: US 9,279,766 B2
(45) Date of Patent: Mar. 8, 2016

(54) INFORMATION TERMINAL DEVICE AND OBJECT IDENTIFICATION DEVICE

(75) Inventors: Masaru Matsuoka, Osaka (JP); Takashi Watanabe, Osaka (JP); Tetsuhiro Kaya, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 302 days.

(21) Appl. No.: 14/129,285

(22) PCT Filed: Jul. 27, 2012

(86) PCT No.: PCT/JP2012/004806
§ 371 (c)(1),
(2), (4) Date: Dec. 25, 2013

(87) PCT Pub. No.: WO2013/018342
PCT Pub. Date: Feb. 7, 2013

(65) Prior Publication Data
US 2014/0146640 A1 May 29, 2014

(30) Foreign Application Priority Data
Aug. 4, 2011 (JP) .................. 2011-170677

(51) Int. Cl.
*G01N 21/55* (2014.01)
*G01S 15/02* (2006.01)
*G02F 1/1333* (2006.01)
*G02F 1/1335* (2006.01)
*H03K 17/96* (2006.01)
*G09G 5/00* (2006.01)
*G02F 1/133* (2006.01)

(52) U.S. Cl.
CPC .............. *G01N 21/55* (2013.01); *G01S 15/02* (2013.01); *G02F 1/1336* (2013.01); *G02F 1/13338* (2013.01); *G09G 5/00* (2013.01); *H03K 17/9631* (2013.01); *G02F 2001/13312* (2013.01); *G09G 2330/12* (2013.01); *G09G 2354/00* (2013.01); *G09G 2360/145* (2013.01)

(58) Field of Classification Search
CPC ................. G02F 1/13338; G02F 2001/13312; G02F 1/1336; H03K 17/9631; G01S 15/02; G09G 2354/00; G09G 5/00; G09G 2330/12; G01N 21/55
See application file for complete search history.

(56) References Cited

U.S. PATENT DOCUMENTS

2014/0146640 A1* 5/2014 Matsuoka ........... G02F 1/13338
367/95

FOREIGN PATENT DOCUMENTS

| JP | 06-177737 | * | 8/1994 |
| JP | 2003-090987 A | | 3/2003 |

(Continued)

OTHER PUBLICATIONS

International Search Report of PCT Application No. PCT/JP2012/004806.

*Primary Examiner* — Daniel Pihulic
(74) *Attorney, Agent, or Firm* — Shinjyu Global IP

(57) ABSTRACT

An information terminal device (100) comprises a light source (171) that directs light at a display face on which a display component (110) is disposed, an object detecting sensor (170) that receives light from the display face, and a controller (300) that determines whether or not a sheet (180) has been affixed to the display face on the basis of the output from the object detecting sensor (170).

12 Claims, 5 Drawing Sheets

(56) References Cited

FOREIGN PATENT DOCUMENTS

| | | | | |
|---|---|---|---|---|
| JP | 2004302229 A | * | 10/2004 | |
| JP | 2007334527 A | * | 12/2007 | |
| JP | 2009179409 A | * | 8/2009 | |
| WO | WO 2013018342 A1 | * | 2/2013 | .......... G02F 1/13338 |

* cited by examiner

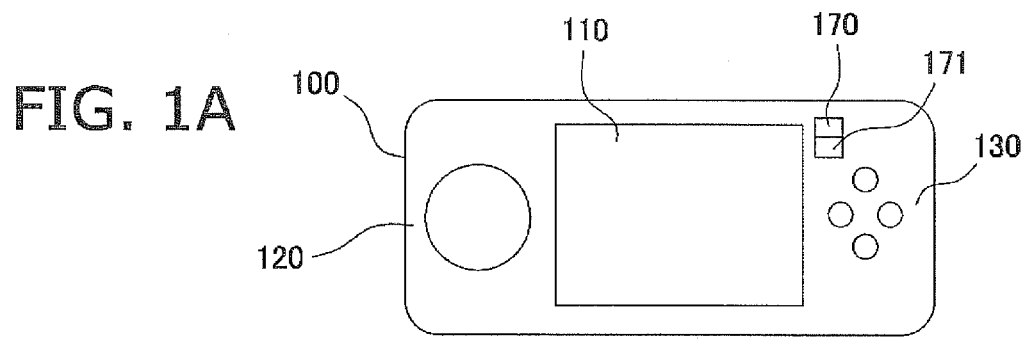
FIG. 1A
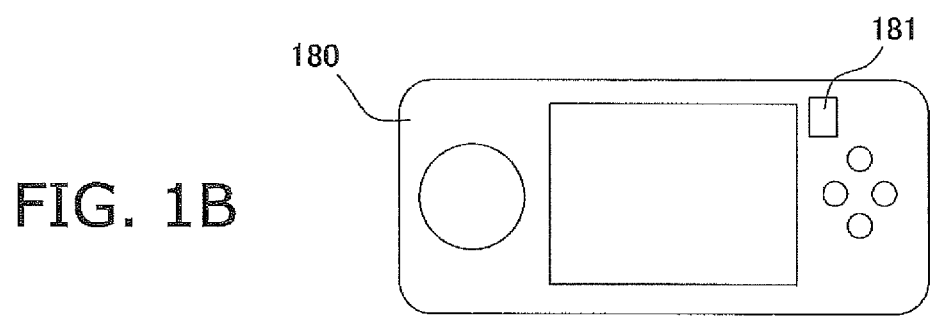
FIG. 1B
FIG. 2
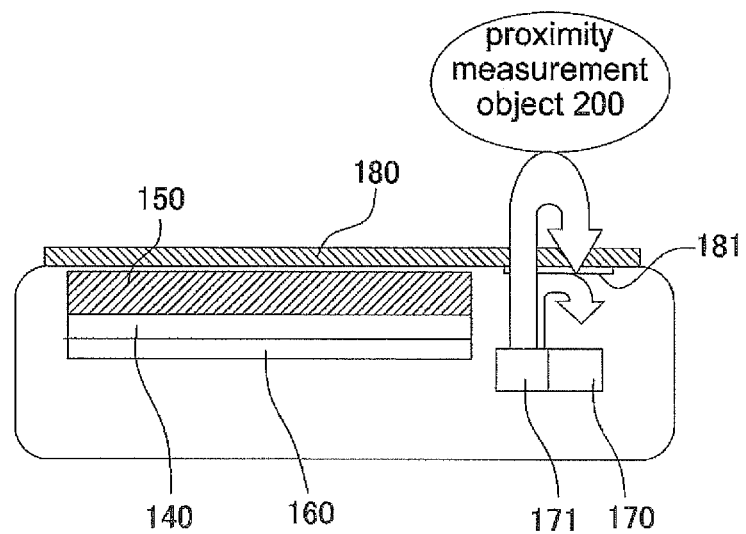

INFORMATION TERMINAL DEVICE AND OBJECT IDENTIFICATION DEVICE

PRIORITY

This application claims priority International Application PCT/JP2012/004806, with an international filing date of Jul. 27, 2012 which claims priority to Japanese Patent Application No. 2011-170677 filed on Aug. 4, 2011. The entire disclosures of International Application PCT/JP2012/004806 and Japanese Patent Application No. 2011-170677 are hereby incorporated herein by reference.

TECHNICAL FIELD

The technology disclosed herein relates to an information terminal device to which a film is affixed.

BACKGROUND

Information terminal devices that are used in aircraft, trains, automobiles, and other such moving vehicles need to have a film affixed to a monitor surface in order to prevent the shattering of glass or other materials used in the monitor, to ensure the safety of passengers in the event of a collision. This anti-shatter film has been made of a transparent material that has an even thickness and transmits visible light, so as not to affect input to a touch panel or the visibility of the display panel that lies underneath this. However, the film may be worn off or intentionally peeled off, or a worker may forget to affix it at the manufacturing stage of the information terminal device, so particularly with aircraft, the crew would conduct an inspection, but it took time to confirm whether the film was really there because it was made of a transparent material.

Japanese Laid-Open Patent Application 2003-90987, for example, discusses a way to easily detect that a film made of a transparent material has been peeled off. What Patent Literature 1 discloses allows the user to use a recognition mark attached to the film to check for peeling of a protective film that is supposed to be removed in the manufacturing process. This recognition mark can be checked by eye or with an image processing device to prevent the film from being accidentally applied twice or prevent part of the film from remaining after peeling.

SUMMARY

However, the invention disclosed in Japanese Laid-Open Patent Application 2003-90987 involves confirming the peeling of a protective film that is supposed to be removed in the manufacturing process, and since this film is removed during manufacture, it is alright if the recognition mark is there. On the other hand, an anti-shatter film is required during the use of an information terminal device, and a recognition mark would mar the appearance, and could get in the way of viewing the display panel during use.

The technology disclosed herein provides an information terminal device with which it is easy to confirm whether or not an anti-shatter film has been peeled off.

The information terminal device disclosed herein comprises a display component that displays information, a light emitting component that directs light at a display face on which the display component is disposed, a light receiving component that receives light from the display face, and a controller that determines whether or not a sheet has been affixed to the display face on the basis of the output from the light receiving component.

With the information terminal device disclosed herein, it can be detected that a film has been peeled off.

BRIEF DESCRIPTION OF THE DRAWINGS

FIGS. 1A and 1B are plan views of an exemplary information terminal device

FIG. 2 is a cross section of an exemplary information terminal device

DETAILED DESCRIPTION

Figure 3A:
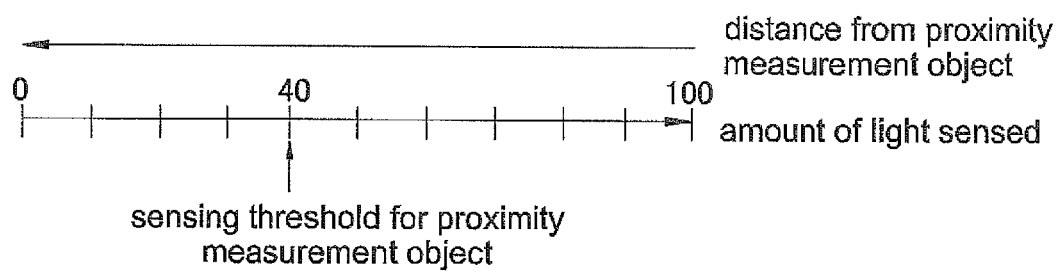
FIGS. 3A and 3B are concept diagrams of the relation between the amount of light sensed by an object detecting sensor and the distance to a proximity measurement object

Selected embodiments of information terminal device 100 will be described through reference to the drawings. It will be apparent to those skilled in the art from this disclosure that the following descriptions of the embodiments are provided for illustration only and not for the purpose of limiting the invention as defined by the appended claims and their equivalents.

Embodiment 1

Configuration of Information Terminal Device 100

FIG. 1 is a plan view of the information terminal device 100. FIG. 2 is a cross section of the information terminal device 100. FIG. 3 is a concept diagram of the relation between the amount of light sensed by an object detecting sensor 170 and the distance to a proximity measurement object 200.

FIG. 1a shows the information terminal device 100 when no film 180 has been affixed, and FIG. 1b shows the film 180. The film 180 is affixed to the information terminal device 100, but the separate drawings are given to aid in description.

The information terminal device 100 is a compact terminal used in an aircraft, a train, an automobile, or another such moving vehicle. With the information terminal device 100, for example, AV content provided by a server inside the moving vehicle (an example of an external device; not shown) is reproduced, or conversation with the crew, etc., is carried out.

In FIG. 1, the information terminal device 100 has a transmitter 120 and a receiver 130 disposed on the left and right, flanking a display component 110 in the middle. The transmitter 120 is a microphone, and the receiver 130 is a speaker. The display component 110 has a liquid crystal panel 140 (an example of a display panel), a transparent glass touch panel 150 (an example of a cover) disposed over the liquid crystal panel 140, and a backlight 160 (an example of a light emitting component).

The backlight 160 is disposed inside the casing of the information terminal device 100. The backlight 160 emits light from below onto the liquid crystal panel 140. A video image is displayed on the liquid crystal panel 140 when the AV content is reproduced, and reproduction and other such instructions are received at the touch panel 150. The touch panel 150 is used for not only instructions such as AV content reproduction, but various kinds of input by touching the control keys displayed on the liquid crystal panel 140 with a finger or the like.

The object detecting sensor 170 (an example of a light receiving component) is disposed near the receiver 130. The object detecting sensor 170 is disposed on the receiver 130 side of the display component 110. In the example shown in FIG. 1, the object detecting sensor 170 is disposed between the display component 110 and the receiver 130. However, the object detecting sensor 170 is disposed inside the casing of the information terminal device 100.

The purpose of the object detecting sensor 170 is to prevent accidental input when the user's ear or cheek touches the touch panel 150 in the use of the transmitter 120 and the receiver 130 to perform communication. The object detecting sensor 170 senses that the user's ear or cheek is moving closer to the touch panel 150, and prevents accidental input by deactivating input with the touch panel 150.

The object detecting sensor 170 is integrated with a light source 171 (an example of a light emitting component). The object detecting sensor 170 receives light that comes out of the light source 171 and is reflected by a proximity measurement object 200 (such as a human ear or cheek), and measures the amount of reflected light, thereby detecting that an object has approached. As will be discussed below, the object detecting sensor 170 can detect that the film 180 has not been affixed if light reflected by the film 180 cannot be detected.

The anti-shatter film 180 is affixed so as to cover both the touch panel 150 and the object detecting sensor 170. The purpose of affixing the anti-shatter film 180 is to prevent the touch panel 150 from cracking and shattering in the event that a passenger, etc., should bump into the glass touch panel 150, and thereby ensure better safety.

The film 180 in this embodiment covers the entire face of the flat part of the information terminal device 100, but at a minimum should cover the touch panel 150 and the object detecting sensor 170 or the light source 171.

Light emitted from the backlight 160 is controlled by the liquid crystal panel 140, and passes through the touch panel 150 and the film 180. If the reflection coefficient of the visible light band is high for the touch panel 150 and the film 180 here, the brightness of the display component 110 will drop, and visibility will suffer.

The portion of the film 180 that covers the object detecting sensor 170 is treated to make the reflection coefficient for light (infrared light, visible light, or other light in a particular wavelength band) different from that of other portions, as a reflection coefficient change component 181. More specifically, the reflection coefficient change component 181 can be formed by one of the following methods.

For example, this method may involve affixing an optical film that reflects light of a wavelength that can be sensed by the object detecting sensor 170, or it may involve affixing a resin or coating with a pigment that reflect light of a wavelength that can be sensed by the object detecting sensor 170. In other words, the method should involve raising the reflection coefficient of light at the reflection coefficient change component 181 over the reflection coefficient of light at the film 180.

With the information terminal device 100 to which the film 180 has been affixed, the relation between proximity and the amount of reflected light is measured at a plurality of points while a person's hand or the like, for example, is moved from close to the object detecting sensor 170 to farther away, during the design or manufacture of the device. This data is then stored as a lookup table in the information terminal device 100, so that the proximity corresponding to an amount of reflected light can be found. If the usage mode is such that it is detected when the proximity measurement object 200 has moved closer than a specific distance, the amount of reflected light sensed at the specific distance is set as a first threshold TH1, and the device is set to sense that the proximity measurement object 200 has approached when an amount of reflected light that exceeds this first threshold TH1 is sensed.

Also, the amount of light reflected by the film 180 out of all the light emitted from the light source 171 is measured in a situation in which the proximity measurement object 200 is not close to the object detecting sensor 170 during the design or manufacture of the information terminal device 100 to which the film 180 has been affixed. This measured value is stored on a recording medium or a server. This measured value is then set as a second threshold TH2 in the information terminal device 100, and the device is set to detect that no film 180 has been affixed when an amount of reflected light that is below this second threshold TH2 is sensed.

The operation of detecting peeling of the anti-shatter film 180 in the information terminal device 100 of this embodiment configured as above will be described through reference to FIGS. 2 and 3.

In FIG. 2, light emitted from the light source 171 is transmitted by the film 180, but some of the light is reflected by the reflection coefficient change component 181, which has a high reflection coefficient, and enters the object detecting sensor 170.

If the light transmitted (not reflected) by the reflection coefficient change component 181 is reflected by the proximity measurement object 200, it enters the object detecting sensor 170. As discussed above, when an amount of reflected light that exceeds the first threshold TH1 is sensed, it is detected that the proximity measurement object 200 has approached.

FIG. 3a shows the relation between the amount of light sensed by the object detecting sensor 170 of a conventional information terminal device, and the distance to the proximity measurement object 200. In FIG. 3a, if we let the amount of light coming out of the light source 171 be "100," the amount of reflected light sensed by the object detecting sensor 170 approaches the maximum value of 100 when the proximity measurement object 200 is sufficiently close to the object detecting sensor 170. However, if the proximity measurement object 200 is a person's face, etc., there may be variance in the reflection coefficient of the surface (such as between a white person and a black person), so the threshold for detecting that the object has approached is set to about "40" to allow a margin of error.

Thus, with a conventional configuration, if the proximity measurement object 200 goes past the threshold of proximity object detection ("40" in FIG. 3a), the object detecting sensor 170 can detect that the proximity measurement object 200 is nearby. Below the above threshold of "40," the object detecting sensor 170 can detect that the proximity measurement object 200 is not nearby.

Figure 3B:
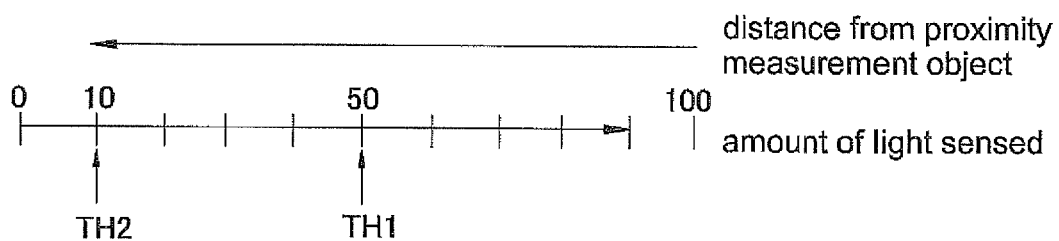

Next, FIG. 3b shows the relation between the amount of light sensed by the object detecting sensor 170 of the information terminal device 100 in this embodiment, and the distance to the proximity measurement object 200.

First, as discussed above, with the information terminal device 100, the amount of light sensed by the object detecting sensor 170 when the proximity measurement object 200 is sufficiently far away, that is, the amount of light reflected by the reflection coefficient change component 181, is set to the second threshold TH2 that indicates whether or not there is a film 180. In this embodiment, the second threshold TH2 is set to "10." During use, the second threshold TH2 is compared to the amount of light sensed by the object detecting sensor 170.

Meanwhile, the first threshold TH1, at which it is detected that the proximity measurement object 200 is close, is set to "50," which takes into account the second threshold TH2. The maximum value for the amount of light sensed is reduced to "90" because part of the light is reflected by the reflection coefficient change component 181 of the film 180 when the reflected light is incident, but this is sufficient with respect to the "50" that is the first threshold TH1 serving as the benchmark for detecting proximity. When an amount of light is sensed that exceeds "50" (the first threshold TH1), the information terminal device 100 can detect that the proximity measurement object 200 is nearby. If the film 180 is peeled off, rather than the proximity measurement object 200 in front of the information terminal device 100, the amount of light sensed by the object detecting sensor 170 will be under "10" (the second threshold TH2), and the information terminal device 100 can detect that the film 180 has been peeled off.

The information terminal device 100 can display information to the effect that the film has been peeled, on the liquid crystal panel 140 or another such display portion, and thereby convey this information to an inspector, user, crew member, or the like. Also, the information terminal device 100 can send this information (that the film has been peeled) to a server, and thereby notify a manufacturing manager, repair technician, or the like. This helps eliminate defective products and makes repair more efficient.

Thus, a single object detecting sensor 170 can be used to detect the distance or proximity of the proximity measurement object 200, and to detect the peeling of the film 180.

Functional Configuration of Controller 300

Figure 4:
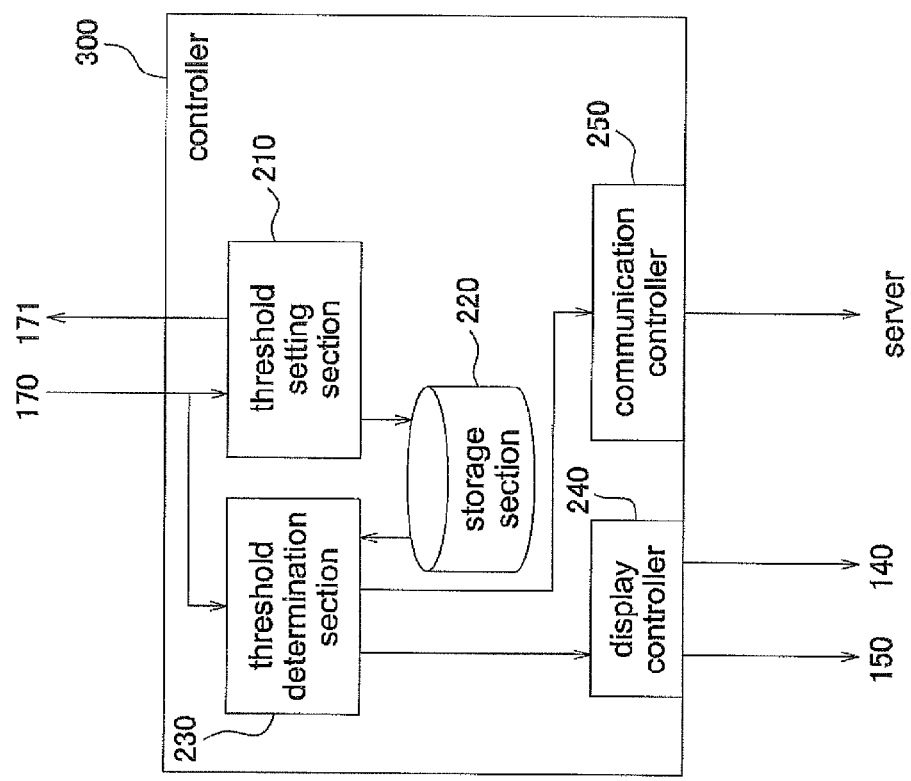
FIG. 4 is a block diagram of an exemplary functional configuration of the controller

The functional configuration of a controller 300 built into the information terminal device 100 will be described through reference to the drawings. FIG. 4 is a block diagram of the functional configuration of the controller 300.

The controller 300 comprises a threshold setting section 210, a storage section 220, a threshold determination section 230, a display controller 240, and a communication controller 250.

The threshold setting section 210 sets the first threshold TH1 serving as the benchmark for detecting the proximity of the proximity measurement object 200, and the second threshold TH2 serving as the benchmark for detecting the peeling of the film 180.

First, the threshold setting section 210 causes the light source 171 to emit light every time the distance of the proximity measurement object 200 from the object detecting sensor 170 on the manufacturing line is changed in stages. The threshold setting section 210 acquires the amount of reflected light detected by the object detecting sensor 170 every time light is emitted from the light source 171. This amount of reflected light includes not only the amount of light reflected by the proximity measurement object 200, but also the amount of light reflected by the film 180. The threshold setting section 210 produces a lookup table listing the relation between the amount of reflected light and the distance of the proximity measurement object 200, and stores this table in the storage section 220. The threshold setting section 210 refers to the lookup table to set the amount of reflected light corresponding to a specific distance (such as about 10 cm) to the first threshold TH1.

Then, the threshold setting section 210 causes the light source 171 to emit light without moving the proximity measurement object 200 closer to the object detecting sensor 170 on the manufacturing line, and acquires the amount of reflected light detected by the object detecting sensor 170. This amount of reflected light is the amount of light reflected by the film 180, and does not include the amount of light reflected by the proximity measurement object 200. The threshold setting section 210 sets the amount of light reflected by the film 180 to the second threshold TH2.

Next, the threshold setting section 210 stores the first threshold TH1 and the second threshold TH2 in the storage section 220.

The threshold determination section 230 acquires in real time the amount of reflected light RL detected by the object detecting sensor 170. The threshold determination section 230 refers to the storage section 220 to acquire the first threshold TH1 and the second threshold TH2. The threshold determination section 230 determines the magnitude relation between the amount of reflected light RL and the first threshold TH1, and the magnitude relation between the amount of reflected light RL and the second threshold TH2. If the amount of reflected light RL is greater than the first threshold TH1, the threshold determination section 230 sends a message to that effect to the display controller 240. If the amount of reflected light RL is less than the second threshold TH2, the threshold determination section 230 sends a message to that effect to the display controller 240 and the communication controller 250.

The display controller 240 deactivates the touch panel 150 when a message to the effect that the amount of reflected light RL is greater than the first threshold TH1 has been received from the threshold determination section 230. Consequently, the information terminal device 100 does not react if the user's ear or cheek touches the touch panel 150.

Also, the display controller 240 displays a warning on the liquid crystal panel 140 when a message to the effect that the amount of reflected light RL is less than the second threshold TH2. Examples of this warning include text or images indicating that the protective film has been peeled off. On the manufacturing line, an inspector will see the warning displayed on the liquid crystal panel 140, making it easy to recognize that no film 180 is affixed to the information terminal device 100.

The communication controller 250 is connected to a server installed in a moving vehicle (an aircraft, a train, an automobile, etc.) when the information terminal device 100 is installed in a moving vehicle. The communication controller 250 sends the server a warning to the effect that the protective film has been peeled off when a message to the effect that the amount of reflected light RL is less than the second threshold TH2 has been received from the threshold determination section 230. Here, the communication controller 250 may send the individual information about the information terminal device 100 along with the warning. In an actual usage environment, this notification from the communication controller 250 would make it easy for a crew member or manager to recognize that the film 180 has been peeled off of the information terminal device 100.

Operation of Controller 300

Figure 5:
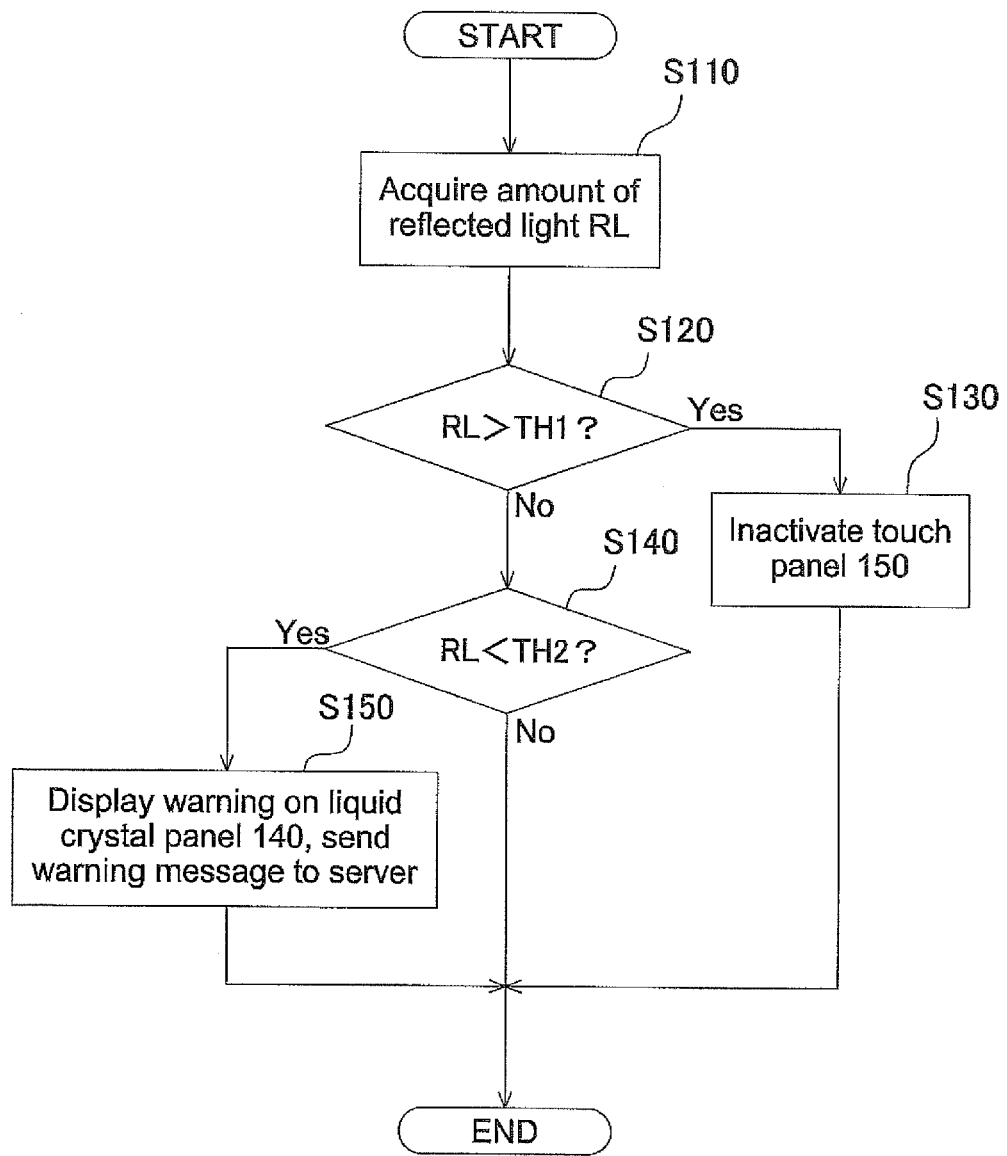
FIG. 5 is a flowchart of an exemplary operation of the controller

The operation of the controller 300 will be described through reference to the drawings. FIG. 5 is a flowchart of the operation of the controller 300. In the following description, we will assume that the first threshold TH1 and the second threshold TH2 have already been set.

In step S110, the controller 300 acquires the amount of reflected light RL detected by the object detecting sensor 170.

In step S120, the controller 300 determines whether or not the amount of reflected light RL is greater than the first threshold TH1. If it is determined that the amount of reflected light RL is greater than the first threshold TH1, the processing proceeds to step S130. If it is determined that the amount of reflected light RL is not greater than the first threshold TH1, the processing proceeds to step S140.

In step S130, the controller 300 deactivates the touch panel 150 in response to the fact that the amount of reflected light RL is greater than the first threshold TH1. The controller 300 then temporarily ends processing, and repeats the processing from step S110.

In step S140, the controller 300 determines whether or not the amount of reflected light RL is less than the second threshold TH2. If it is determined that the amount of reflected light RL is less than the second threshold TH2, the processing proceeds to step S150. If it is determined that the amount of reflected light RL is not less than the second threshold TH2, the controller 300 temporarily ends processing, and repeats the processing from step S110.

In step S150, the controller 300 sends the server and displays on the liquid crystal panel 140 a message to the effect that the protective film has been peeled off, in response to the fact that the amount of reflected light RL is less than the second threshold TH2.

Embodiment 2

An information terminal device 100A pertaining to Embodiment 2 will be described through reference to the drawings. What is different from Embodiment 1 is that the object detecting sensor does not detect the proximity of an object, and that a backlight is used as a light source. The following description will focus on the differences from Embodiment 1, and those components that are shared with Embodiment 1 will be numbered the same and will not be described again.

Figure 6:
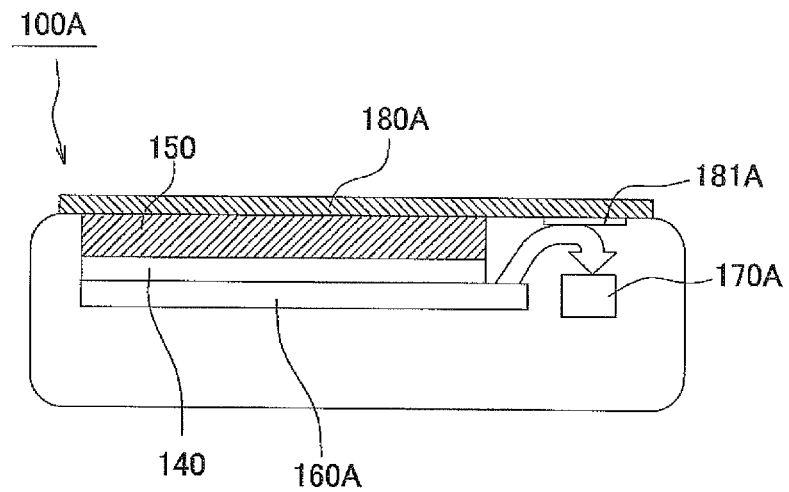
FIG. 6 is a cross section of an exemplary information terminal device

FIG. 6 is a cross section of the configuration of the information terminal device 100A. As shown in FIG. 6, the information terminal device 100A comprises a backlight 160A, an object detecting sensor 170A, and a film 180A.

The backlight 160A emits light at the liquid crystal panel 140. Part of the light from the backlight 160A is emitted toward the film 180A. Specifically, the backlight 160A is used as a light source for detecting whether or not there is a film 180A.

The object detecting sensor 170A detects the amount of reflected light that is emitted from the backlight 160A and reflected by a reflection coefficient change component 181A. If the amount of reflected light detected by the object detecting sensor 170A is greater than a specific value, it can be detected that the film 180A has been properly affixed. On the other hand, if the amount of reflected light detected by the object detecting sensor 170A is not greater than the specific value, it can be detected that the film 180A has not been affixed. The specific value can be determined by using the amount of light reflected by the film 180A as a reference.

The film 180A covers the touch panel 150 and the object detecting sensor 170A. The reflection coefficient change component 181A is provided to the film 180A. The reflection coefficient change component 181A preferably has the characteristic of reflecting light emitted from the backlight 160A.

With the information terminal device 100A having the above configuration, whether or not the film 180A has been properly affixed can be easily detected according to the amount of reflected light detected by the object detecting sensor 170A.

Embodiment 3

An information terminal device 100B pertaining to Embodiment 3 will be described through reference to the drawings. What is different from Embodiment 1 is that the object detecting sensor does not detect the proximity of an object, and that the light source is disposed outside of the casing. The following description will focus on the differences from Embodiment 1, and those components that are shared with Embodiment 1 will be numbered the same and will not be described again.

Figure 7:
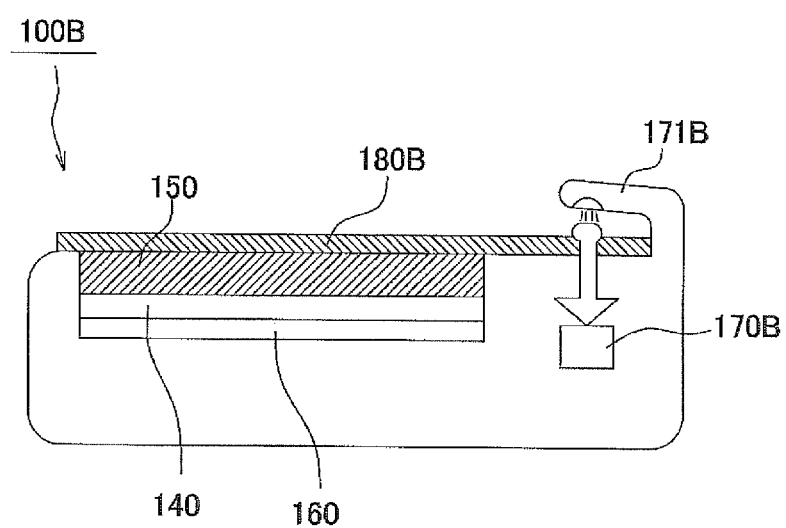
FIG. 7 is a cross section of an exemplary information terminal device

FIG. 7 is a cross section of the configuration of the information terminal device 100B. As shown in FIG. 7, the information terminal device 100B comprises an external light source 171B, an object detecting sensor 170B, and a film 180B.

The external light source 171B is disposed on the outside of the casing of the information terminal device 100B. The external light source 171B can emit light (light of a particular wavelength band, such as infrared light or visible light) toward the object detecting sensor 170B.

The object detecting sensor 170B detects the amount of light that is emitted from the external light source 171B and transmitted by the film 180B. If the amount of light detected by the object detecting sensor 170B is less than a specific value, it can be detected that the film 180B has been properly affixed. On the other hand, if the amount of light detected by the object detecting sensor 170B is greater than a specific value, it can be detected that no film 180B has been affixed. The specific value can be determined by using as a reference the remainder obtained by subtracting the amount of light absorbed or reflected by the film 180B from the amount of light emitted from the external light source 171B.

The film 180B covers the touch panel 150 and the object detecting sensor 170B. In the example shown in FIG. 7, no reflection coefficient change component is formed in the film 180B. However, if the amount of light absorbed or reflected by the film 180B is small, the detection accuracy of the object detecting sensor 170B can be improved by coating the film 180B with a pigment or the like to increase the amount of light absorbed or reflected by the film 180B.

With the information terminal device 100B having the above configuration, whether or not the film 180B has been properly affixed can be easily detected according to the amount of reflected light detected by the object detecting sensor 170B.

Other Embodiments (A) In the above embodiment, the reflection coefficient change component 181 simultaneously covered the object detecting sensor 170 (light receiving component) and the light source 171, but may instead cover only the object detecting sensor 170 or the light source 171. This will suppress a reduction in the maximum value of the amount of light sensed, and expand the width of the threshold for detecting that the proximity measurement object 200 is nearby.

(B) In the above embodiment, whether or not there was a film was detected by detecting with the object detecting sensor the light emitted from the light source, but this is not the only option. Whether or not there is a film may be detected by using a sound wave sensor to detect sound waves or ultrasonic waves outputted from a sound source. In this case, the sound waves or ultrasonic waves reflected by the film may be detected with a sound wave sensor, or sound waves or ultrasonic waves that have passed through the film may be detected by a sound wave sensor.

(C) In the above embodiment, the touch panel 150 was given as an example of a cover that covers at least part of the surface of the liquid crystal panel 140, but this is not the only option. A glass sheet or the like can be used instead of the touch panel 150 as the cover.

(D) Although not directly touched upon in the above embodiment, it is preferable for the light source or the object detecting sensor to be surrounded by a wall. This reduces accidental detection by the object detecting sensor of light reflected by some other member inside the casing.

(E) Although not directly touched upon in the above embodiment, it is preferable for the light source or the object detecting sensor to be close to the film. This reduces accidental detection by the object detecting sensor of light reflected by some other member inside the casing.

(F) Although not directly touched upon in the above embodiment, it is preferable for the reflection coefficient change component to have a filter function that will selectively reflect light of a wavelength that can be sensed by the sensor.

(G) In the above embodiment, a message to the effect that no sheet was affixed was displayed on the display component or sent to the server, but this is not the only option. For instance, the fact that no sheet is affixed may be conveyed by issuing a warning sound from a speaker. The fact that a sheet is affixed may also be conveyed to the display component or a server.

INDUSTRIAL APPLICABILITY

With the information terminal device disclosed herein, the peeling of a film can be automatically detected, which is useful in the field of information terminal devices.

GENERAL INTERPRETATION OF TERMS

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of the information terminal device and object identification device. Accordingly, these terms, as utilized to describe the technology disclosed herein should be interpreted relative to the information terminal device and object identification device.

The term "configured" as used herein to describe a component, section, or part of a device includes hardware and/or software that is constructed and/or programmed to carry out the desired function.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicants, including the structural and/or functional concepts embodied by such feature(s). Thus, the foregoing descriptions of the embodiments according to the present invention are provided for illustration only, and not for the purpose of limiting the invention as defined by the appended claims and their equivalents.

The invention claimed is:

1. An information terminal device, comprising:
a display component that displays information;
a light emitting component that directs light at a display face on which the display component is disposed;
a light receiving component that receives light from the display face; and
a controller that determines whether or not a sheet has been affixed to the display face on the basis of the output from the light receiving component.

2. The information terminal device according to claim 1, wherein the light emitting component and the light receiving component are disposed inside the device.

3. The information terminal device according to claim 1, wherein the display component further comprises a display panel for displaying information, and a cover that covers at least part of the surface of the display panel, and the sheet covers the surface of the cover.

4. The information terminal device according to claim 1, wherein the sheet changes the reflection coefficient of light for part of the light receiving component periphery from that of the other parts.

5. The information terminal device according to claim 1, wherein the sheet has a filter function so that light of a wavelength that can be sensed by the light receiving component is selectively reflected.

6. The information terminal device according to claim 1, wherein a notification is made on the basis of the result of determining whether or not the sheet has been affixed.

7. The information terminal device according to claim 1, wherein result of determining whether or not the sheet has been affixed is displayed on the display panel.

8. The information terminal device according to claim 6, further comprising a communication component that communicates with an external device,
wherein the result of determining whether or not the sheet has been affixed is transmitted through the communication component to the external device.

9. The information terminal device according to claim 1, wherein the light receiving component detects the distance from an object located at the outside of the device by receiving light reflected by the object.

10. An object discrimination device, comprising:
a display component that displays information;
a light emitting component that directs light at a display face on which the display component is disposed;
a light receiving component that receives light from the display face; and a controller that determines whether or not a sheet has been affixed to the display face on the basis of the output from the light receiving component.

11. An information terminal device, comprising:

a display component that displays information;

a sound source that directs sound waves at a display face on which the display component is disposed;

a sound wave detector that detects sound waves from the display face; and a controller that determines whether or not a sheet has been affixed to the display face on the basis of the output from the sound wave detector.

12. The information terminal device according to claim 2, wherein the light receiving component detects the distance from an object located at the outside of the device by receiving light reflected by the object.

* * * * *